US012089880B2

(12) United States Patent
Predick et al.

(10) Patent No.: US 12,089,880 B2
(45) Date of Patent: Sep. 17, 2024

(54) SPINE IMPLANT WITH AN EXPANDABLE CAGE AND EXPANDABLE VERTEBRAL ATTACHMENT PLATE

(71) Applicant: LIFE SPINE, INC., Huntley, IL (US)

(72) Inventors: Daniel P. Predick, Wheat Ridge, CO (US); Randall F. Dryer, Austin, TX (US); Garrett D. Lauf, Hampshire, IL (US)

(73) Assignee: LIFE SPINE, INC., Huntley, IL (US)

( * ) Notice: Subject to any disclaimer, the term of this patent is extended or adjusted under 35 U.S.C. 154(b) by 74 days.

(21) Appl. No.: 17/957,125

(22) Filed: Sep. 30, 2022

(65) Prior Publication Data

US 2023/0027836 A1 Jan. 26, 2023

Related U.S. Application Data

(63) Continuation of application No. 17/181,058, filed on Feb. 22, 2021, now Pat. No. 11,457,957.
(Continued)

(51) Int. Cl.
*A61F 2/44* (2006.01)
*A61B 17/70* (2006.01)
*A61B 17/80* (2006.01)

(52) U.S. Cl.
CPC ...... *A61B 17/7059* (2013.01); *A61B 17/8023* (2013.01); *A61B 17/8047* (2013.01); *A61F 2/447* (2013.01)

(58) Field of Classification Search
CPC ....... A61B 17/80–8095; A61B 17/7059; A61F 2/44–447
See application file for complete search history.

(56) References Cited

U.S. PATENT DOCUMENTS 6,093,205 A * 7/2000 McLeod ................. A61F 2/442
606/279
10,299,934 B2 * 5/2019 Seifert ................... A61F 2/4455
(Continued)

FOREIGN PATENT DOCUMENTS

WO WO-2014/113003 A1 7/2014

OTHER PUBLICATIONS

International Search Report and Written Opinion on PCT PCT/US2021/019164 dated Jun. 8, 2021.

*Primary Examiner* — Eduardo C Robert
*Assistant Examiner* — Steven J Cotroneo
(74) *Attorney, Agent, or Firm* — Foley & Lardner LLP

(57) ABSTRACT

A spine implant for receipt between and fastened to a lower vertebra and an adjacent upper vertebra is characterized by an expandable cage and an expandable plate attached to the expandable cage. When the expandable cage is expanded, both the expandable cage and the expandable plate expand together at a uniform rate of movement. Engagement features of the expandable cage cooperate with engagement features of the expandable plate such that expansion of the expandable cage carries the expandable plate along during its expansion. The engagement features of the expandable cage may be configured as notches, cavities, or recessed pockets, while the engagement features of the expandable plate may be configured as tangs, flanges, or protuberances styled to be received by the configured notches of the expandable cage. Cam locks on the expandable plate help bone fastener backout.

20 Claims, 11 Drawing Sheets

Related U.S. Application Data

(60) Provisional application No. 63/008,690, filed on Apr. 11, 2020.

(56) References Cited

U.S. PATENT DOCUMENTS

| | | | |
|---|---|---|---|
| 11,457,957 B2* | 10/2022 | Predick | A61B 17/7059 |
| 2004/0193269 A1* | 9/2004 | Fraser | A61B 17/7059 |
| | | | 623/17.11 |
| 2009/0182430 A1* | 7/2009 | Tyber | A61F 2/4465 |
| | | | 606/301 |
| 2011/0144755 A1* | 6/2011 | Baynham | A61F 2/447 |
| | | | 623/17.16 |
| 2014/0277487 A1* | 9/2014 | Davenport | A61F 2/4455 |
| | | | 623/17.16 |
| 2015/0230938 A1 | 8/2015 | Biedermann et al. | |
| 2016/0051374 A1 | 2/2016 | Faulhaber | |
| 2016/0143746 A1* | 5/2016 | Robie | A61F 2/442 |
| | | | 606/71 |
| 2016/0242927 A1* | 8/2016 | Seifert | A61F 2/4425 |
| 2016/0262905 A1 | 9/2016 | Prado et al. | |
| 2017/0119537 A1 | 5/2017 | Tepper et al. | |
| 2017/0172756 A1 | 6/2017 | Faulhaber | |
| 2017/0215930 A1* | 8/2017 | Lauf | A61B 17/7059 |
| 2017/0367842 A1 | 12/2017 | Predick et al. | |
| 2018/0042732 A1 | 2/2018 | Seifert et al. | |
| 2019/0298421 A1* | 10/2019 | Capote | A61F 2/442 |
| 2021/0085482 A1* | 3/2021 | Flickinger | H01L 27/0886 |

* cited by examiner

SPINE IMPLANT WITH AN EXPANDABLE CAGE AND EXPANDABLE VERTEBRAL ATTACHMENT PLATE

CROSS-REFERENCE TO RELATED PATENT APPLICATION

This patent application is a continuation of U.S. patent application Ser. No. 17/181,058, now U.S. Pat. No. 11,457,957, filed on Feb. 22, 2021, which claims benefit of and priority to U.S. Provisional Application No. 63/008,690, filed on Apr. 11, 2020, the entire disclosures of both are hereby incorporated by reference herein.

FIELD OF THE INVENTION

The present invention relates to implants for the spine and, more particularly, to expandable spine implants utilizing supplemental vertebral fixation for stabilizing adjacent vertebrae of the spine.

BACKGROUND OF THE INVENTION

Many people contend with spine issues due to age, disease, trauma, congenital, and acquired complications and conditions. While some spine issues can be alleviated without surgery, other spine issues necessitate surgery. Spine issues such as decompression and stabilization can be addressed with spine (vertebrae) fusion surgery. Spine fusion surgery utilizes an intervertebral or interbody spine implant known as a cage between and attached to the affected adjacent vertebrae. Once disc tissue has been removed from between the affected vertebrae, the cage is placed within the disc space between the adjacent vertebrae. Bone graft may be introduced into the cage for facilitating vertebral bone fusion and stopping movement between adjacent vertebrae. The cage is typically attached to the vertebrae by bone screws.

A desirable outcome of fusion surgery is the maintenance of height of the resulting anatomy relative to the original anatomy while providing a stable and robust spine construct. Restoration of the height of the original spine anatomy of the adjacent vertebrae maintains proper vertebral spacing to help prevent nerve compression, restore and preserve the natural alignment of the spine, and promote spinal fusion. Static (fixed height) or dynamic (adjustable height) cages may be used in the intervertebral space. In the case of a static cage, a particular fixed height cage is used that approximates the original spine anatomy. In the case of a dynamic cage, the original spine anatomy can be better approximated. Because of variations in vertebral anatomy and other issues, it is desirable for intervertebral spine implants (cages) to be adjustable in height (dynamic) rather than fixed in height (static).

Cages may be used alone (i.e. a stand-alone cage) or with supplemental vertebral attachment, such as a spine plate, for additional securement to the affected vertebrae. The spine plate may be dynamic or static. The positioning and securement of the spine implant (the cage and the plate) is important in order to approximate the original vertebral position of the individual and/or to achieve a desired position. It is often difficult during installation to adequately install a dynamic plate relative to a dynamic cage. Other problems may also be encountered during installation.

It is therefore desirous to have a spine implant for spinal fusion of two adjacent vertebrae that provides dynamic sizing. It is further desirous to have a dynamic spine implant having an expandable spine cage for receipt between a lower vertebrae and an adjacent upper vertebrae and an attached expandable spine plate for attachment to the upper and lower vertebrae for vertebral fusion.

SUMMARY OF THE INVENTION

A spine implant is characterized by an expandable cage and an expandable plate that, when connected to each other, expand/move/translate at a uniform rate. This provides concerted alignment of the implant (cage and plate) to the adjacent vertebrae.

The expandable cage has engagement features that provide cooperation with engagement features of the expandable plate. The expandable plate expands with the expansion of the expandable cage at a uniform rate of expansion because the expandable plate is engaged with (connected to) the expandable cage. The expandable plate and expandable cage are also able to controllably collapse/contract/decrease in height at a uniform rate relative to one another. Once expanded however, the cage and plate do not collapse on their own. As shown in the figures, one non-limiting form of the engagement features of the expandable cage may be configured notches, recesses, concavities or pockets (collectively, notches). As also shown in the figures, one non-limiting form of the engagement features of the expandable plate are configured tangs, flanges, hooks, or protuberances (collectively, hooks) styled to cooperate with the configured notches or recessed pockets of the expandable cage.

With the engagement features providing continual engagement of the expandable cage and expandable plate throughout expansion of the expandable cage, the expandable cage also prevents collapsing of the expandable plate under load. Thus, the expandable plate does not require a secondary form of locking translation given its secured engagement to the expandable cage.

The expandable plate will not be allowed to disengage from the expandable cage during movement because during expansion, the engagement features of the expandable plate will be captured between the vertebral bodies and the expandable cage, thus preventing migration.

A locking mechanism may be used to limit or stop movement (translation) of the expandable plate should the expandable plate be used without engaging with the expandable cage. In one form, a threaded locking member is inserted into the expandable plate and upon tightening the locking member at a specific torque, a split pocket of the expandable plate that receives the locking member is cinched together, locking the alternate side of the expandable plate. Various methods may be used to permit and lock plate translation.

The expandable plate is configured to be attached to the lower vertebra via one or more bone fasteners, and to the upper vertebra via one or more bone fasteners.

The spine implant may be used in an anterior lumbar interbody fusion (ALIF) procedure, with or as an anterior cervical plate system (ACPS), or for other spine applications.

Further aspects of the present invention will become apparent from consideration of the drawings and the following description of a form of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The present invention and its features will be better understood by reference to the accompanying drawings, wherein.

Figure 1:
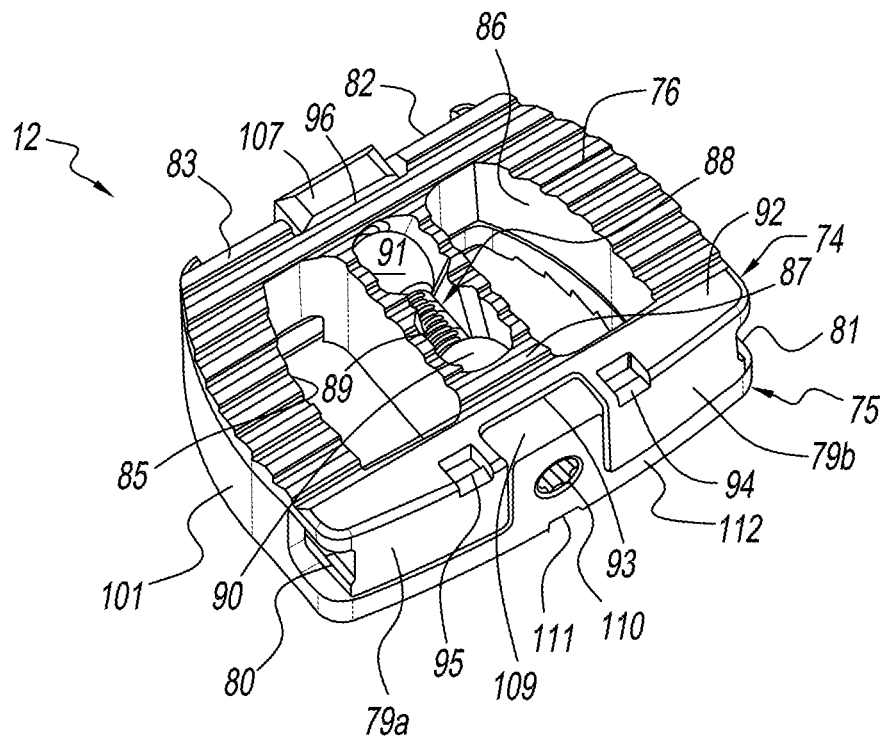
FIG. 1 is a view of an expandable cage of the present spine implant, the expandable cage in an unexpanded position/state.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

DETAILED DESCRIPTION OF THE INVENTION

FIGS. 7-14 depict various views of an expandable spine implant 10 for use as a spine or spinal intervertebral (interbody) device preferably, but not necessarily, for use as part of an Anterior Lumbar Interbody Fusion (ALIF) procedure, as part of an Anterior Cervical Plate System (ACPS), lateral and cervical uses, and/or for other spine applications. The spine implant 10 is characterized by an expandable (and controllably collapsible, but hereinafter "expandable") cage 12 and an expandable (and controllably collapsible, but hereinafter "expandable") plate 14. The expandable cage 12 and the expandable plate 14 are made from a bio-compatible material such as, but not limited to, a metal (e.g. stainless steel, titanium, an alloy of stainless steel, an alloy of titanium), and/or a plastic (e.g. medical grades of PVC and polyethylene, PEEK, polycarbonate, Ultem PEI, polysulfone, polypropylene, polyurethane). The expandable cage 12 and expandable plate 14 may be made via various manufacturing processes known in the art. Both the expandable cage 12 and the expandable plate 14 are vertically (i.e. expandable and collapsible in a cranial/superior to caudal/inferior direction) expandable (and controllably collapsible).

Figure 2:
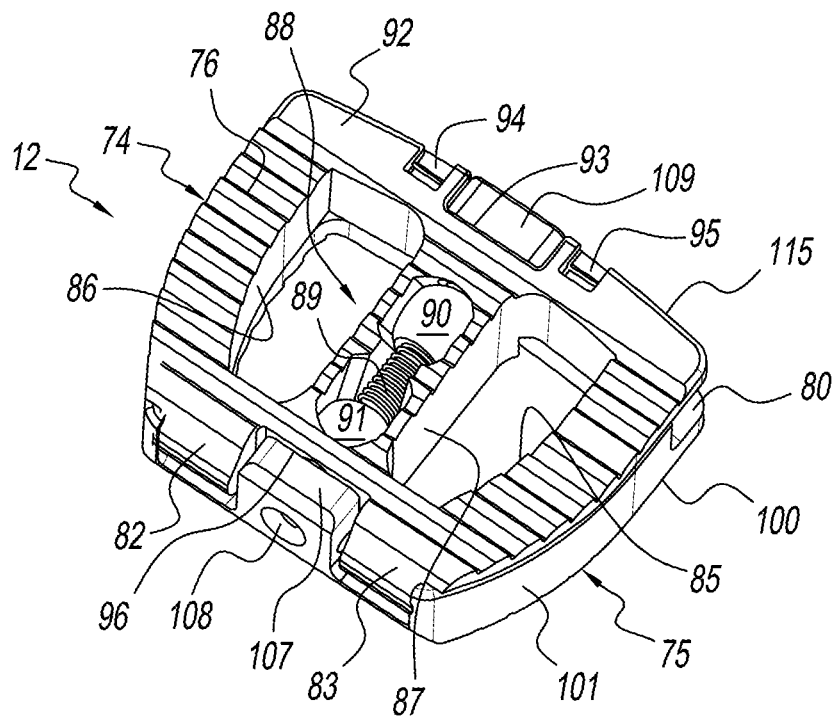
FIG. 2 is another view of the expandable cage of FIG. 1, the expandable cage in the unexpanded position.
Figure 3:
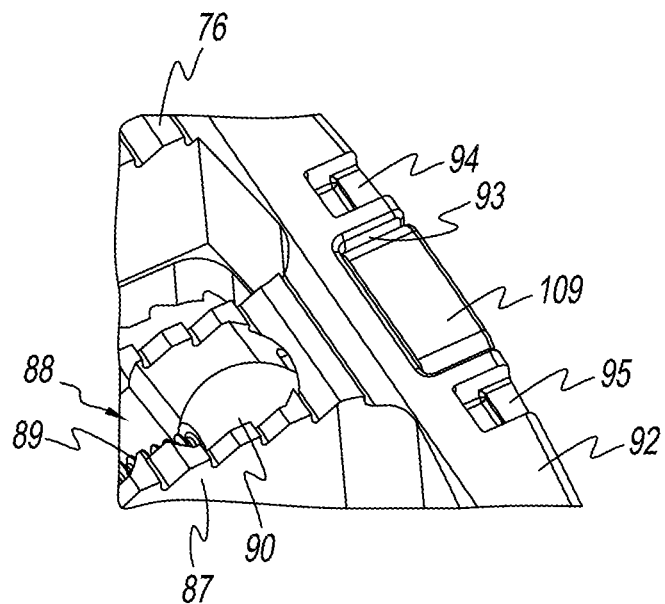
FIG. 3 is an enlarged view of a front area of the expandable cage of FIG. 1.

The expandable cage 12 sans the expandable plate 14 is shown in FIGS. 1-3. In general, the expandable cage 12 has a design overall similar in overall functional attributes as described in US Patent Publication US 2017/0367842 A1 (the '842 Publication), the entire contents of which is specifically incorporated herein by reference, but with novel features that define over the '842 Publication. The expandable cage 12 has a first, lower, inferior, caudal, bottom part, portion, member or the like 75 (collectively and hereinafter, lower member 75) and a second, upper, cranial, superior, or top part, portion, member or the like 74 (collectively and hereinafter, upper member 74). The lower member 75 and the upper member 74 are configured to mesh with one another, and the upper member 74 to move relative to the lower member 75 such that the overall height of the spine implant 10 can increase (expand). The upper member 74 can also decrease (contract/collapse) in height relative to the lower member 75 in order to adjust and set a particular height of the spinal implant 10.

Figure 12:
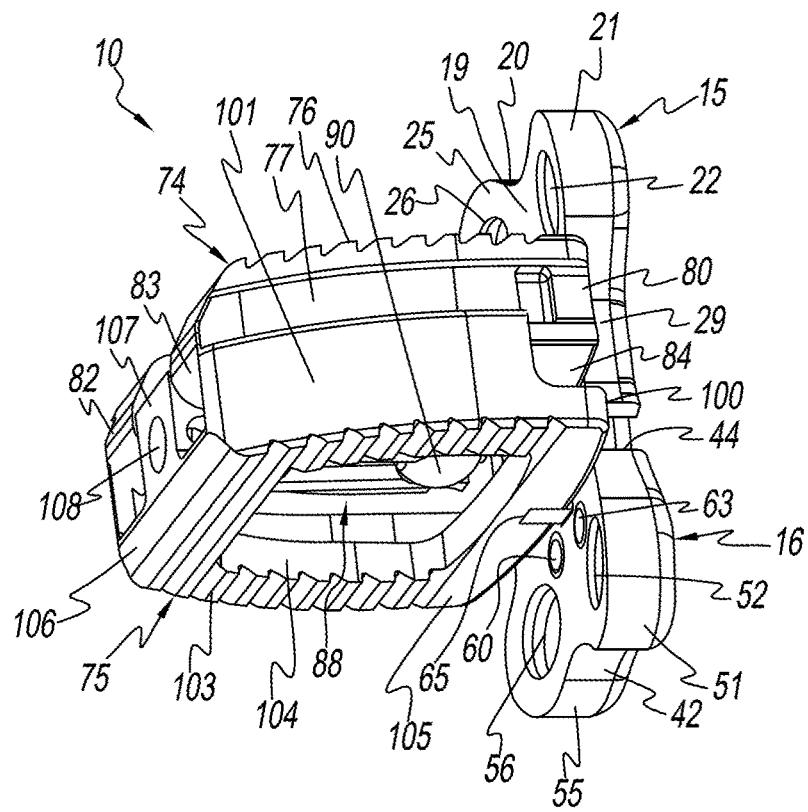
FIG. 12 is a view of the expandable plate engaged with the expandable cage of the present spine implant, both of which are in an expanded position.
Figure 13:
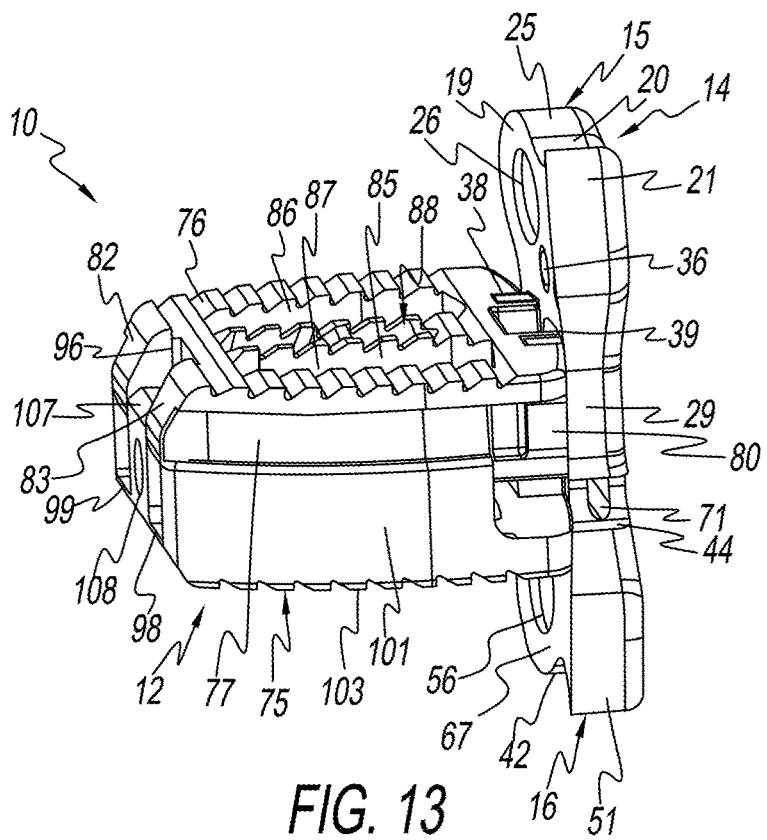
FIG. 13 is a view of the expandable plate engaged with the expandable cage of the present spine implant, both of which are in an expanded position.
Figure 14:
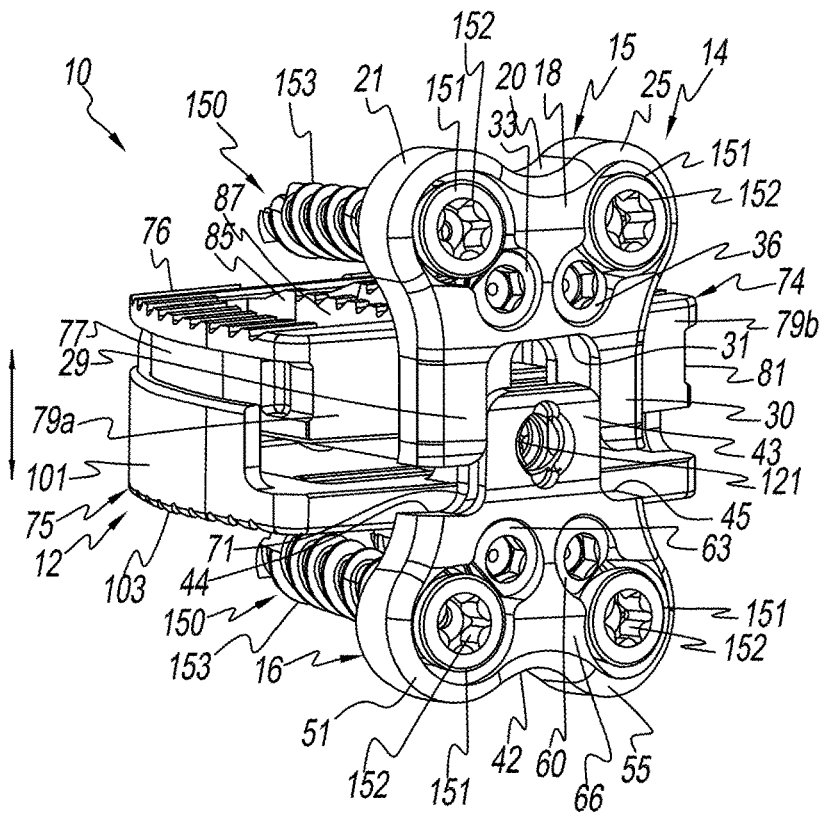
FIG. 14 is a view of the expandable plate engaged with the expandable cage of the present spine implant, both of which are in an expanded position, with bone screws received by the expandable plate.
Figure 15:
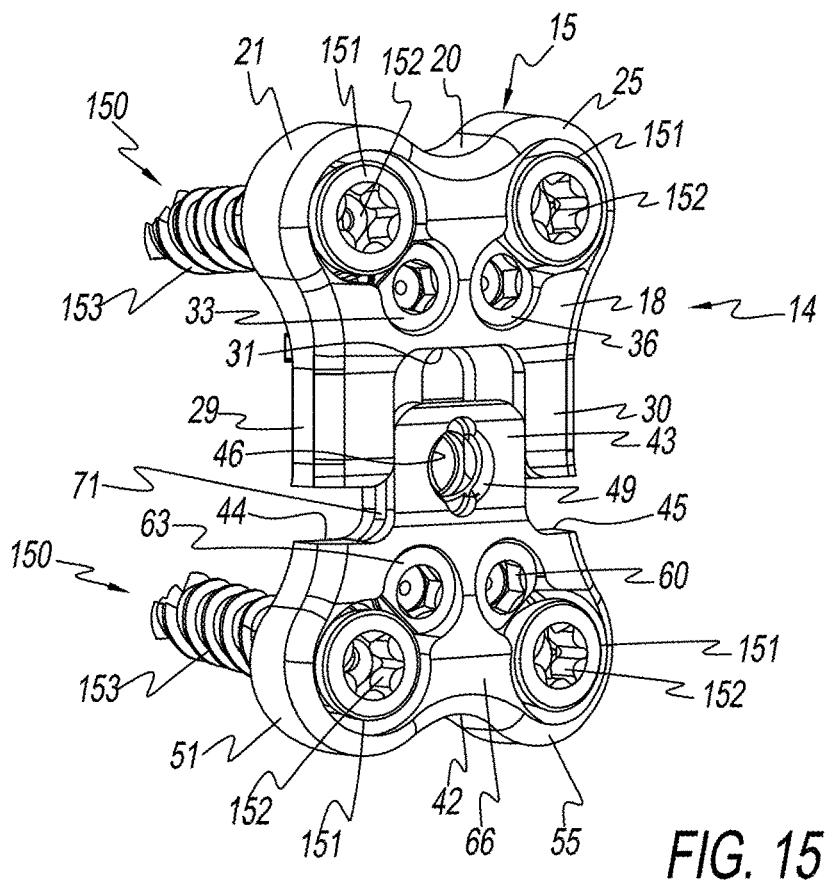
FIG. 15 is a view of the expandable plate in an expanded position with bone screws received by the expandable plate.
Figure 16:
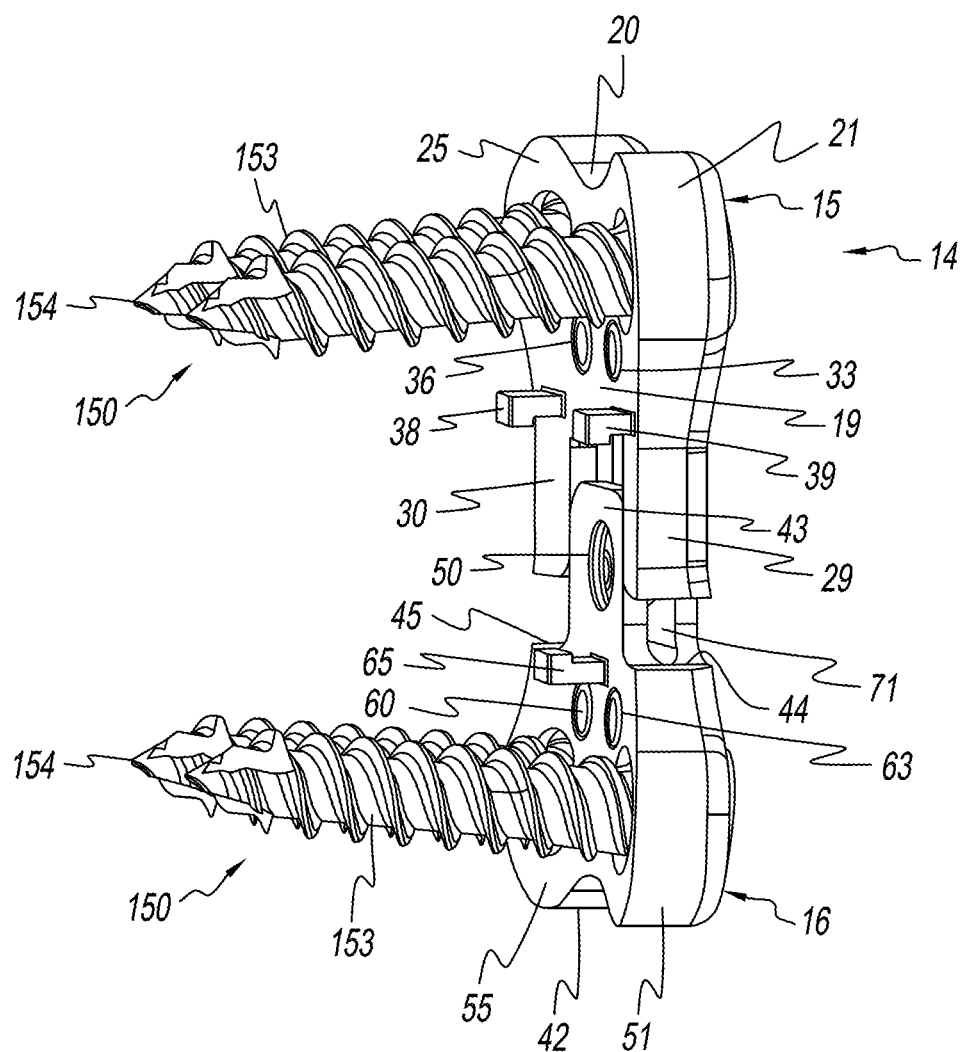
FIG. 16 is a view of the expandable plate in an expanded position with bone screws received by the expandable plate.

The lower member 75 is characterized by a generally rectangular base 100 defining a first lateral side 101, and a second lateral side 102 opposite the first lateral side 101, the nomenclature first and second being arbitrary here, above and throughout unless specifically indicated otherwise. As best seen in FIG. 12, the base 100 preferably, but not necessarily, has a serrated bottom 103 and a central hole 104. A front portion 105 of the bottom 103 is preferably, but not necessarily, without serrations, being generally smooth. The front portion 105 extends generally from the first lateral side 101 to the second lateral side 102. The base 100 also defines a rear 106 with an upstanding generally rectangular projection 107 situated between the first and second lateral sides 101, 102, the projection 107 forming a first area 83 between a first lateral side (not labeled, but implicit) of the projection 107 and the first lateral side 101, and a second area 82 between a second lateral side (not labeled, but implicit) of the projection 107 opposite the first lateral side of the projection 107, and the second lateral side 102. The projection 107 is shown disposed generally midway between the first and second lateral sides 101, 102, but may be positioned otherwise. The rear 106 may be configured differently than shown, such as having two or more projections. The projection 107 has a hole 108 that extends through the projection from one side to the other. The hole 108 may be used for various purposes.

The base 100 also defines a front 112 opposite the rear 106 with an upstanding generally rectangular projection 109 situated between the first and second lateral sides 101, 102 that defines a first pocket 98 between one side of the projection 109 and the first lateral side 101 and a second pocket 99 between a second side of the projection 109 and the second lateral side 102. The projection 109 is shown disposed generally midway between the first and second lateral sides 101, 102, but may be positioned otherwise. The front 112 may be configured differently than shown, such as having two or more projections. The projection 107 has a hole 108 that extends through the projection from one side to the other. The hole 108 may be used for various purposes such as allow access to a socket thereof for manipulating the cage movement (expansion/contraction) mechanism 88. A notch, cutout, cavity, depression or the like 111 is provided in the front of the front portion 105, at the bottom of the projection 109. The notch 111 provides an engagement feature for receipt of an engagement feature of the expandable plate 14, particularly the lower or first portion or member 16, for the base 100. The notch 111 is configured to receive and/or engage with an engagement feature (e.g. hook) of the expandable spine plate 14 and, particularly, the configured hook 65 extending from the backside 67 of the first portion 16 of the expandable plate 14. The notch 111 holds the hook 65 of the first portion 16 so that the first portion 16 does not move with respect to the base 100 of the expandable cage 12.

The upper member 74 of the expandable cage 12 is characterized by a generally rectangular body 115 having a top 76 with serrations or the like covering its majority with the exception of a front strip or area 92 at the front of the body 115 that extends from the first lateral side 77 to the second lateral side 78, a first lateral side 77, a second lateral side 78 opposite the first lateral side 77, the nomenclature first and second being arbitrary, a front that is generally divided into a first front portion 79a proximate the first lateral side 77 and a second front portion 79b proximate the second lateral side 78, and a rear defined by a first flange 83 situated proximate to the first lateral side 77 and a second flange 82 situated proximate the second lateral side 78. The first flange 83 is sized for reception in the first area 98 of the base 100, while the second flange 82 is sized for reception in the second area 99 of the base 100. The first area 98 provides a channel for reception and movement therein of the first flange 83, while the second area 99 provides a channel for reception and movement therein of the second flange 82, such that the upper member 74 is axially moveable up and down in and relative to the lower member 75. An area 93 is defined between the first front portion 79a and the second front portion 79b of the upper member 74 that is sized and configured to receive the flange 109 of the lower member 75.

The upper member 74 further includes a first front nook, cutout, cavity or the like 80 disposed at a first lateral end (not labeled) of the first front portion 79a proximate the first lateral side 101 of the base 100, and a second front nook, cutout, cavity or the like 81 disposed at a second lateral end (not labeled) of the second front portion 79b proximate the second lateral side 102 of the base 100. The front end of the first lateral side 101 is configured to allow access to the first front nook 80, while the front end of the second lateral side 102 is configured to allow access to the second front nook 81. The first and second nooks 80, 81 are used to receive an installation instrument/tool (not shown) to aid in implanting/placement of the expandable cage 12.

Figure 7:
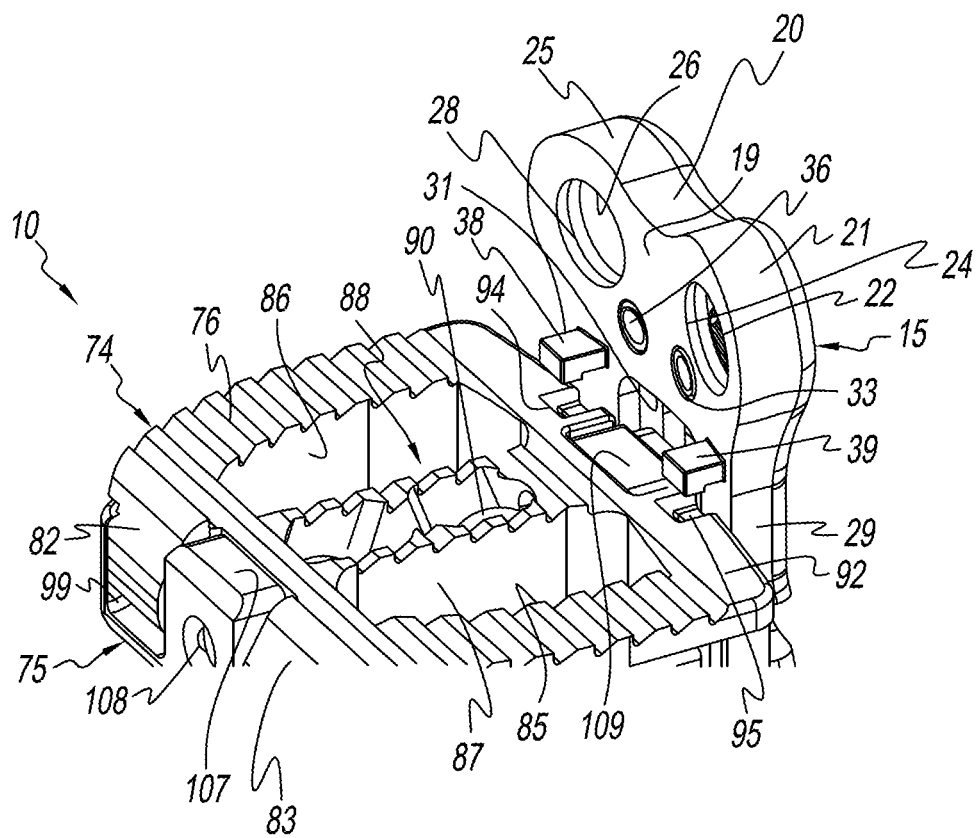
FIG. 7 is a view of a portion of the expandable cage in an unexpanded position showing the expandable plate unengaged relative to the expandable plate.
Figure 8:
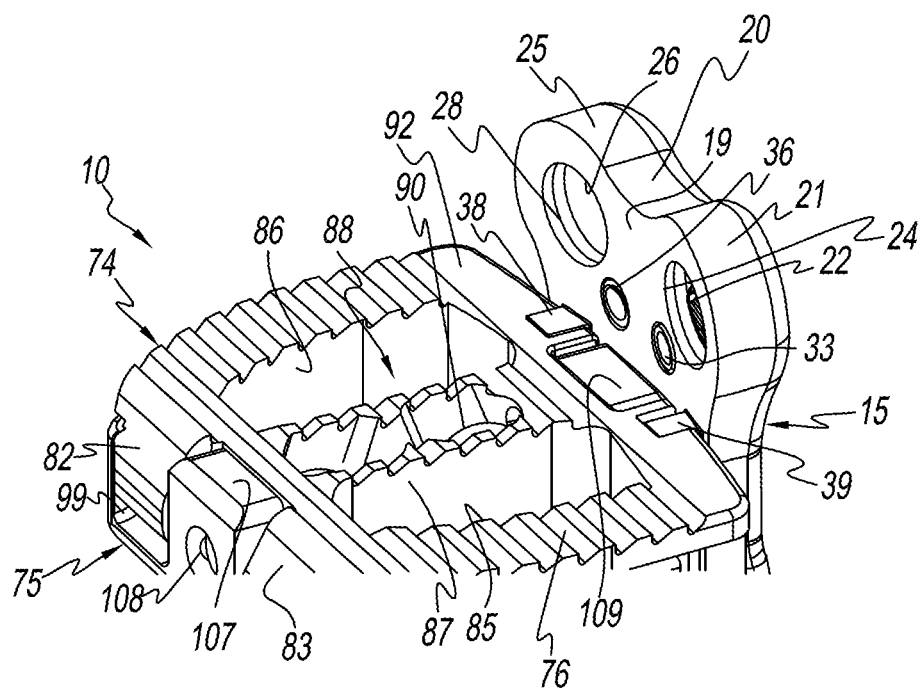
FIG. 8 is a view of the portion of the expandable cage of FIG. 7 with the expandable plate engaged with the expandable cage, the expandable plate in an unexpanded position.
Figure 9:
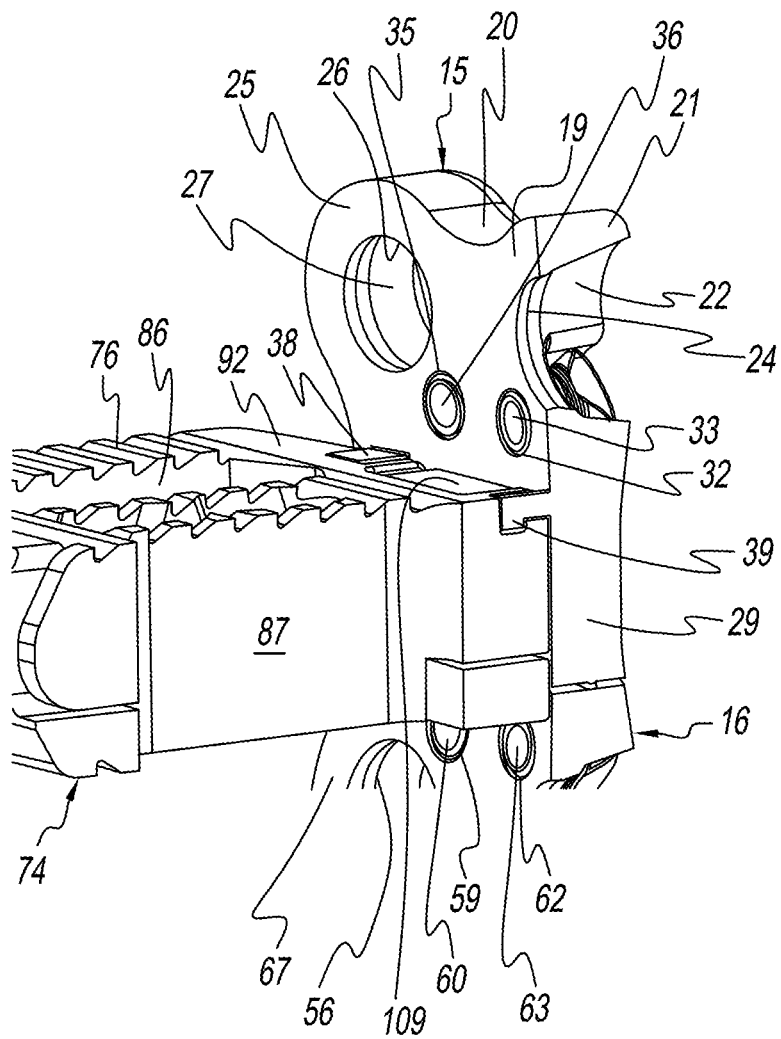
FIG. 9 is an enlarged view of the portion of the expandable cage of FIG. 7 with the expandable plate engaged with the expandable cage, both of which are in an unexpanded position.

The upper member 74 further includes engagement features for the expandable plate 14, particularly the second or upper portion 15 of the expandable plate 14. A first notch, cutout, cavity, depression or the like 95 is provided in the top of the strip 92 at the intersecting edge of the strip 92 and the first front portion 79a proximate to one side of the area 93. A second notch, cutout, cavity, depression or the like 94 is provided in the top of the strip 92 at the intersecting edge of the strip 92 and the second front portion 79b proximate to another side of the area 93. The first and second notches 95, 94 provides a spine plate engagement feature for the upper member 74. The first and second notches 95, 94 are configured to receive and/or engage with engagement features of the expandable plate 14 and, particularly and respectively, with a first configured hook 39 extending from a backside 29 of the second portion 15 of the expandable plate 14, and a second configured hook 38 extending from the backside 29 of the second portion 15 of the expandable plate 14. As illustrated in FIGS. 7-9, the notches 95, 94 hold the hooks 39, 38 of the second or upper plate portion or member 15 so that the second plate portion 15 does not move with respect to the lower or first plate portion or member 14.

As best seen in FIGS. 1-3, 7-8, and 12, the movement or drive structure 88 for expanding and contracting the expandable cage 12 will now be described, but reference is made to the '842 Publication for a manner of achieving cage expansion and contraction, which can be used for the present expandable cage 12 and, explains in greater detail how the present movement structure 88 works in like manner thereto. The body 115 of the upper portion 74 of the expandable cage 12 includes a middle section 87 extending from the front to the rear of the body 115. The middle section 87 defines a first opening 85 at one lateral side of the middle section 87, and a second opening 86 at an opposite lateral side of the middle section. The openings in the upper and lower members 74, 75 aid, promote and/or assist in bone ingrowth with or without bone graft. The middle section 87 maintains the movement structure 88 that allows for axial movement between the upper member 74 and the lower member 75 to cause the expandable cage 12 to expand and collapse (contract).

A first rotation element 90 is provided at the front of the middle section 87, while a second rotation element 91 is provided at the rear of the middle section 87. A threaded shaft 89 connects the first and second rotation elements 90, 91. The threaded shaft 89 is accessible via the hole 108 of the flange 107 of the lower member 75. Rotation of the threaded shaft 89 causes the first and/or second rotation elements 90, 91 to move (raise/expand and lower/contract) the upper member 74 relative to the lower member 75. FIGS. 1 and 2, e.g., show the expandable cage 12 only, with the upper member 74 thereof in a non-expanded or un-raised position relative to the lower member 75 thereof. FIGS. 11-14, e.g., show the expandable cage 12 in an expanded or raised position relative to the lower member 75. The expandable plate 14 is also shown in FIGS. 11-14, e.g., connected to the expandable cage 12 via the hooks 38, 39 of the second portion 15 engaging the notches 94, 95 of the upper member 74 of the expandable cage 12, and the hook 65 engaging the notch 111 of the lower member 75 of the expandable cage 12.

Figure 4:
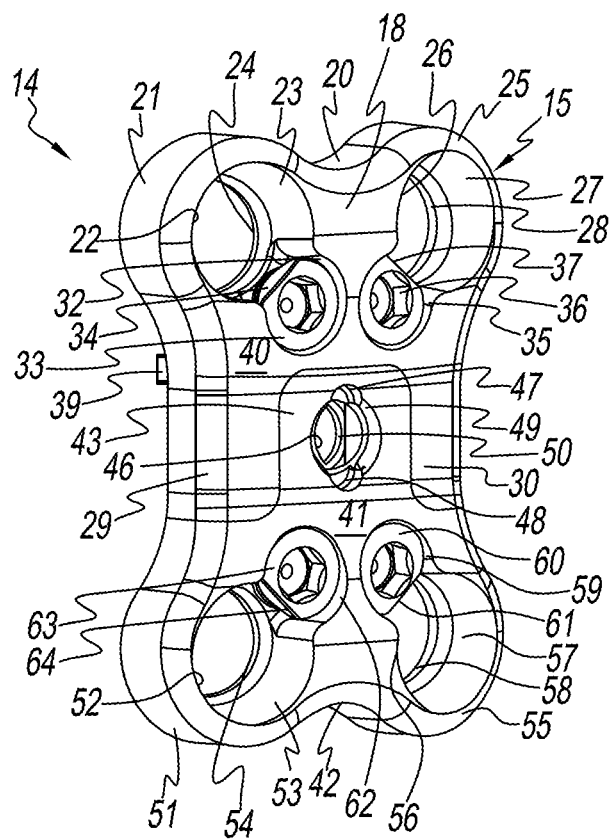
FIG. 4 is a front view of an expandable plate of the present spine implant in an unexpanded position.
Figure 5:
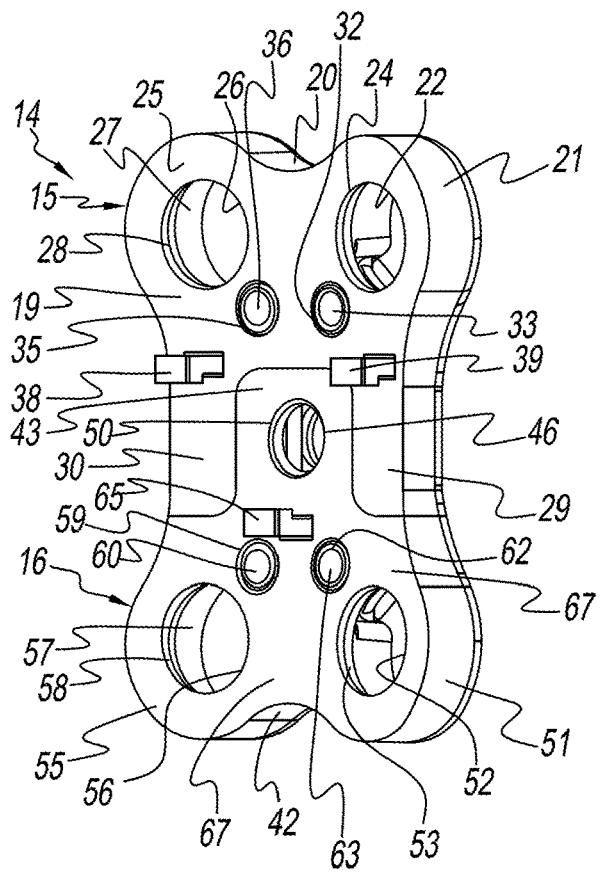
FIG. 5 is a rear view of the expandable plate of FIG. 4 in the unexpanded position.
Figure 6:
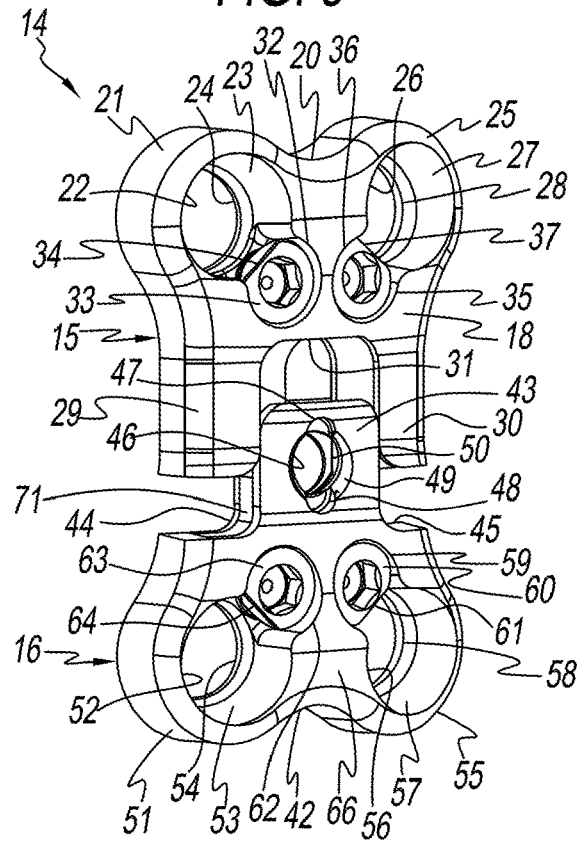
FIG. 6 is a front view of the adjustable plate of FIG. 4, the adjustable plate in an expanded position.

The expandable plate 14 is shown in FIGS. 4-6. In general the expandable plate 14 has a design that is overall similar, but not the same, in overall functional attributes as described in US Patent Publication US 2017/0215930 A1, the entire contents of which is specifically incorporated herein by reference—but with novel features that define the expandable plate 14 over the '930 Publication. In FIG. 4, the expandable plate 14 is shown in a non-expanded position and from the front thereof. In FIG. 5, the expandable plate 14 is shown in a non-expanded position and from the back thereof. In FIG. 6, the expandable plate 14 is shown from the front in an expanded position wherein the first and second portions 15, 16 are separated from each other.

The expandable plate 14 has a second portion, segment, member, part, component or the like 15 and a first portion, segment, member, part, component or the like 16, the second portion 15 may be considered an upper portion while the first portion 16 may be considered a lower portion, the upper portion 15 configured for engagement with the upper member 74 of the expandable cage 12, and the lower portion 16 configured for engagement with the lower member 75 of the expandable cage 12.

Figure 20:
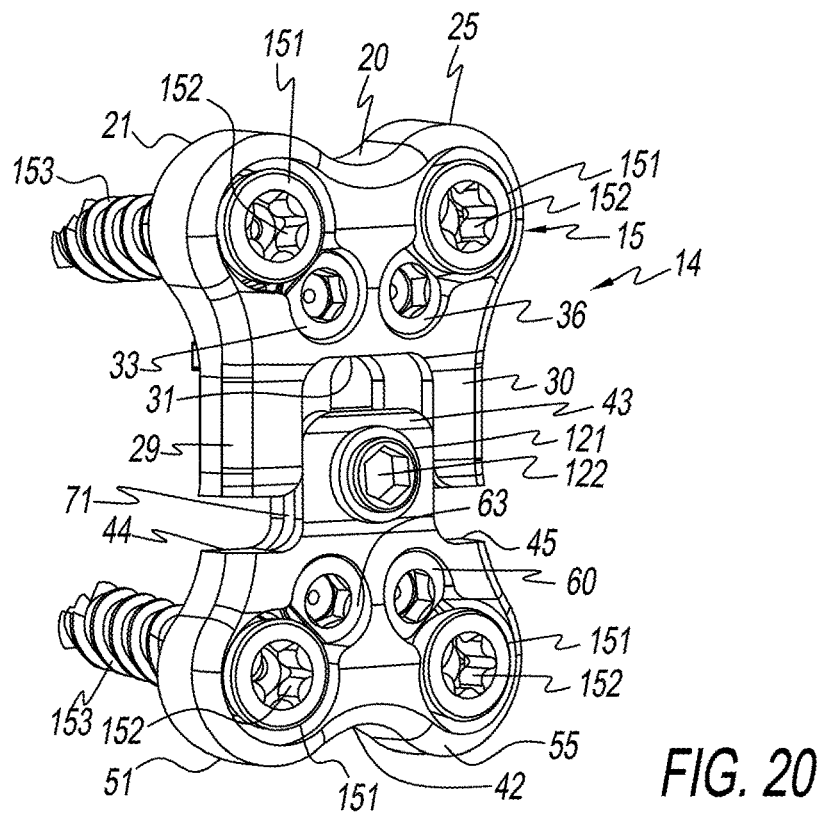
FIG. 20 is a view of the expandable plate in an expanded position with bone screws received by the expandable plate and a threaded locking member received by the expandable plate.

The second portion 15 is configured for attachment to vertebral bone of an upper vertebra (not shown) and is characterized by a generally flat body 40 defining a generally flat front 18, a generally flat rear 19, and a curved top 20. A first boss 21 is formed at a first top corner while a second boss 25 is formed at a second top corner opposite the first top corner. A first boss bore 22 extends through the first boss 21 and is configured for reception and retention of a bone screw 150. The first boss bore 22 includes internal threading 24 for meshing with the threading 155 about the underside of the head 151 of the bone screw 150. A countersink 23 is provided in the front 18 surrounding the first boss bore 22 for reception of the bone screw head 151. In order to aid and/or assist in retaining the bone screw 150 in the first boss bore 22, and/or to prevent or inhibit bone screw back-out, a locking member 33 is provided in a hole 32 in the front 18 of the second portion 15 adjacent the first boss bore 22. The locking member 33 is rotatable in the hole 32 via an instrument or tool (not shown) that is received in a configured socket (as seen in the Figures) of the locking member 33. The locking member 33 is generally round with a flat 34 on one side thereof. The hole 32 and thus the locking member 33 are closely adjacent the first boss bore 22 and thus the head 151 of a bone screw 150. When the locking member 33 is rotated such that the flat 34 is adjacent the first boss bore 22 and thus adjacent the head 151 of a bone screw 150, (see, e.g. FIG. 20), the head 151 and thus the bone screw 150 can freely pass by the locking member 33. This allows the bone screw 150 to be removed from the first boss bore 22 or received in the first boss bore 22. When the flat 34 is rotated away from the first boss bore 22 and thus the head 151 of the bone screw 150, the head of the locking member 33 extends over the head 151 of the bone screw 150 such the head 151 and thus the bone screw 150 cannot freely pass by the locking member 33 and out of the first boss bore 22. This locks the bone screw 150 in place relative to the second portion 15.

A second boss bore 26 extends through the second boss 25 and is configured for reception and retention of a bone screw 150. The second boss bore 26 includes internal threading 28 for meshing with the threading 155 about the underside of the head 151 of the bone screw 150. A countersink 27 is provided in the front 18 surrounding the second boss bore 26 for reception of the bone screw head 151. In order to aid and/or assist in retaining the bone screw 150 in the second boss bore 26, and/or to prevent or inhibit bone screw back-out, a locking member 36 is provided in a hole 35 in the front 18 of the second portion 15 adjacent the second boss bore 26. The locking member 36 is rotatable in the hole 35 via an instrument or tool (not shown) that is received in a configured socket (as seen in the Figures) of the locking member 36. The locking member 36 is generally round with a flat 37 on one side thereof. The hole 35 and thus the locking member 36 are closely adjacent the second boss bore 26 and thus the head 151 of a bone screw 150. When the locking member 36 is rotated such that the flat 37 is adjacent the second boss bore 26 and thus adjacent the head 151 of a bone screw 150, (see, e.g. FIG. 20), the head 151 and thus the bone screw 150 can freely pass by the locking member 36. This allows the bone screw 150 to be removed from the second boss bore 26 or received in the second boss bore 26. When the flat 37 is rotated away from the second boss bore 26 and thus the head 151 of the bone screw 150, the head of the locking member 36 extends over the head 151 of the bone screw 150 such the head 151 and thus the bone screw 150 cannot freely pass by the locking member 36 and out of the second boss bore 26. This locks the bone screw 150 in place relative to the second portion 15.

Axially opposite the curved top 20 of the second portion 15 is a first lateral leg 29 and a second lateral leg 30 each extending axially downward relative to the first and second bosses 21, 25. The first and second lateral legs 29, 30 define a notch, cavity, depression, channel or the like 31 between their laterally inside/inner surfaces (opposite the outer. The channel 31 creates an inner track for reception of at least a part of the first portion 16 as the first and second portions 16, 15 move or expand relative to one another. A first configured hook, tang, flange or the like 38 extends outwardly (transverse) from the rear surface 19 of the second portion 15 and is configured for reception in the notch 94 of the upper portion 74 of the expandable cage 12. A second configured hook, tang, flange or the like 39 extends outwardly (transverse) from the rear surface 19 of the second portion 15 and is configured for reception in the notch 95 of the upper portion 74 of the expandable cage 12.

The first portion 16 is configured for attachment to vertebral bone of a lower vertebra (not shown) and is characterized by a generally flat body 41 defining a generally flat front 66, a generally flat rear 67, and a curved bottom 42. A third configured hook, tang, flange or the like 65 extends outwardly (transverse) from the rear surface 67 of the first portion 16 and is configured for reception in the notch 111 of the lower portion 75 of the expandable cage 12. A third boss 51 is formed at a first bottom corner of the second portion 16 while a fourth boss 55 is formed at a second bottom corner opposite the first bottom corner. A third boss bore 52 extends through the third boss 51 and is configured for reception and retention of a bone screw 150. The third boss bore 52 includes internal threading for meshing with the threading 155 about the underside of the head 151 of the bone screw 150. A countersink 53 is provided in the front 66 surrounding the third boss bore 52 for reception of the bone screw head 151. In order to aid and/or assist in retaining the bone screw 150 in the third boss bore 52, and/or to prevent or inhibit bone screw back-out, a locking member 63 is provided in a hole 62 in the front 66 of the second portion 16 adjacent the third boss bore 52. The locking member 63 is rotatable in the hole 62 via an instrument or tool (not shown) that is received in a configured socket (as seen in the Figures) of the locking member 63. The locking member 63 is generally round with a flat 64 on one side thereof. The hole 62 and thus the locking member 63 are closely adjacent the third boss bore 52 and thus the head 151 of a bone screw 150. When the locking member 63 is rotated such that the flat 64 is adjacent the third boss bore 52 and thus adjacent the head 151 of a bone screw 150, (see, e.g. FIG. 20), the head 151 and thus the bone screw 150 can freely pass by the locking member 63. This allows the bone screw 150 to be removed from the third boss bore 52 or received in the third boss bore 52. When the flat 64 is rotated away from the third boss bore 52 and thus the head 151 of the bone screw 150, the head of the locking member 63 extends over the head 151 of the bone screw 150 such the head 151 and thus the bone screw 150 cannot freely pass by the locking member 63 and out of the third boss bore 52. This locks the bone screw 150 in place relative to the first portion 16.

A fourth boss bore 56 extends through the fourth boss 55 and is configured for reception and retention of a bone screw 150. The fourth boss bore 56 includes internal threading 58 for meshing with the threading 155 about the underside of the head 151 of the bone screw 150. A countersink 57 is provided in the front 66 surrounding the fourth boss bore 56 for reception of the bone screw head 151. In order to aid and/or assist in retaining the bone screw 150 in the fourth boss bore 56, and/or to prevent or inhibit bone screw back-out, a locking member 60 is provided in a hole 59 in the front 66 of the second portion 16 adjacent the fourth boss bore 56. The locking member 60 is rotatable in the hole 59 via an instrument or tool (not shown) that is received in a configured socket (as seen in the Figures) of the locking member 60. The locking member 60 is generally round with a flat 61 on one side thereof. The hole 59 and thus the locking member 60 are closely adjacent the fourth boss bore 56 and thus the head 151 of a bone screw 150. When the locking member 60 is rotated such that the flat 61 is adjacent the fourth boss bore 56 and thus adjacent the head 151 of a bone screw 150, (see, e.g. FIG. 20), the head 151 and thus the bone screw 150 can freely pass by the locking member 60. This allows the bone screw 150 to be removed from the fourth boss bore 56 or received in the fourth boss bore 56. When the flat 61 is rotated away from the fourth boss bore 56 and thus the head 151 of the bone screw 150, the head of the locking member 60 extends over the head 151 of the bone screw 150 such the head 151 and thus the bone screw 150 cannot freely pass by the locking member 60 and out of the fourth boss bore 56. This locks the bone screw 150 in place relative to the first portion 16.

Axially opposite the curved bottom 42 of the second portion 16 is a top flange 43 defining a first lateral notch 44 on a first lateral side of the top flange 43, and a second lateral notch 45 on a second lateral side of the top flange 43 opposite the first lateral notch 45. The flange 43 is sized and/or configured for sliding reception in the notch 31 of the second portion 15. The first lateral notch 44 is sized and configured for sliding receipt of the first lateral leg 29 of the second portion 15. The second lateral notch 45 is sized and configured for sliding receipt of the second lateral leg 30 of the second portion 15. The first lateral notch 44 may include a movement feature 71, shown as a slot or protrusion, for the first lateral leg 29 of the second portion 15. The first lateral leg 29 may include like and/or complementary features. The second lateral notch 45 may includes a movement feature 70, shown as a slot or protrusion for the second lateral leg 30 of the second portion 15. The second lateral leg 30 may include like and/or complementary features. The flange 43 is shown to include a central bore 50 with a countersink 49 formed around the central bore 50. A first inset 47 is formed adjacent an upper area of the central bore 50 while a second inset 48 is formed adjacent a lower area of the central bore.

Figure 10:
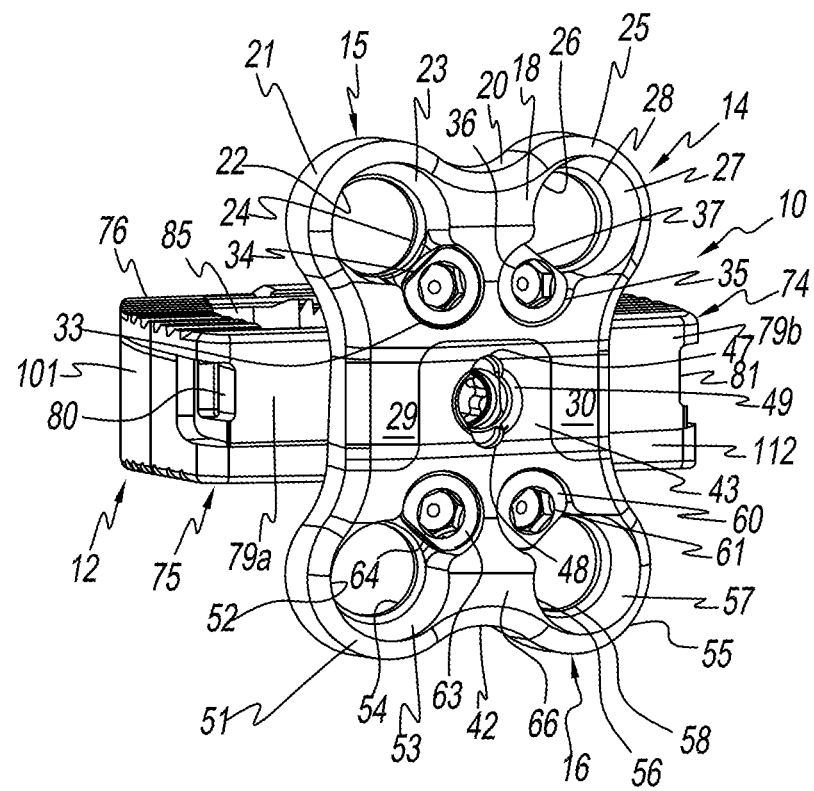
FIG. 10 is a view of the expandable plate engaged with the expandable cage of the present spine implant, both of which are in an unexpanded position.
Figure 11:
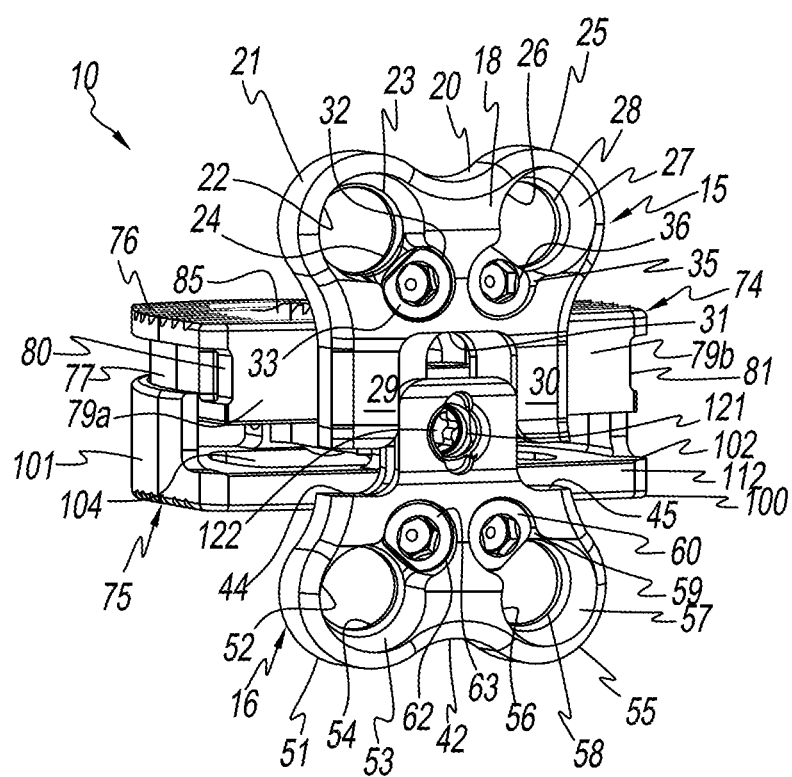
FIG. 11 is a view of the expandable plate engaged with the expandable cage of the present spine implant, both of which are in an expanded position.

FIGS. 11-12 show the expandable plate 14 connected to the expandable cage 12 and in an expanded state. In FIG. 7, the expandable cage 12 has not been expanded so that the hooks 38, 39 of the second portion 15 of the expandable plate 14 have not been received in the notches 94, 95 of the upper section 74 of the expandable cage 12. In FIG. 8, the hooks 38, 39 of the second portion 15 of the expandable plate 14 have been received in the notches 94, 95 of the upper section 74 of the expandable cage 12. FIG. 10 shows an un-expanded cage 12 and an un-expanded plate 14. The various figures show the expandable cage 12 and the expandable plate 14 in expanded and un-expanded positions.

FIGS. 14-20 show the spine implant 10 with bone screws 150 for attaching the expandable plate 14 to vertebral bone of adjacent upper and lower vertebrae (not shown). The bone screws 150 shown are all the same. However, other types and/or shapes of bone screws may be used.

The bone screw 150 is formed of a suitable biocompatible material such as those of the expandable cage 12 and the expandable plate 14 as described above, and is made in a same or similar manner. The bone screw 150 is characterized by a threaded shaft 153 having a head 151 at one end of the threaded shaft 153 and a generally pointed tip 154 at an opposite end of the threaded shaft. The head 151 includes a socket or hole 152 configured to receive an installation tool (not shown) having a complementary portion that is received in the socket 122. The underside of the head 151 has external threading that is configured to mesh with the threading of the bone screw holes of the expandable plate 14.

Figure 17:
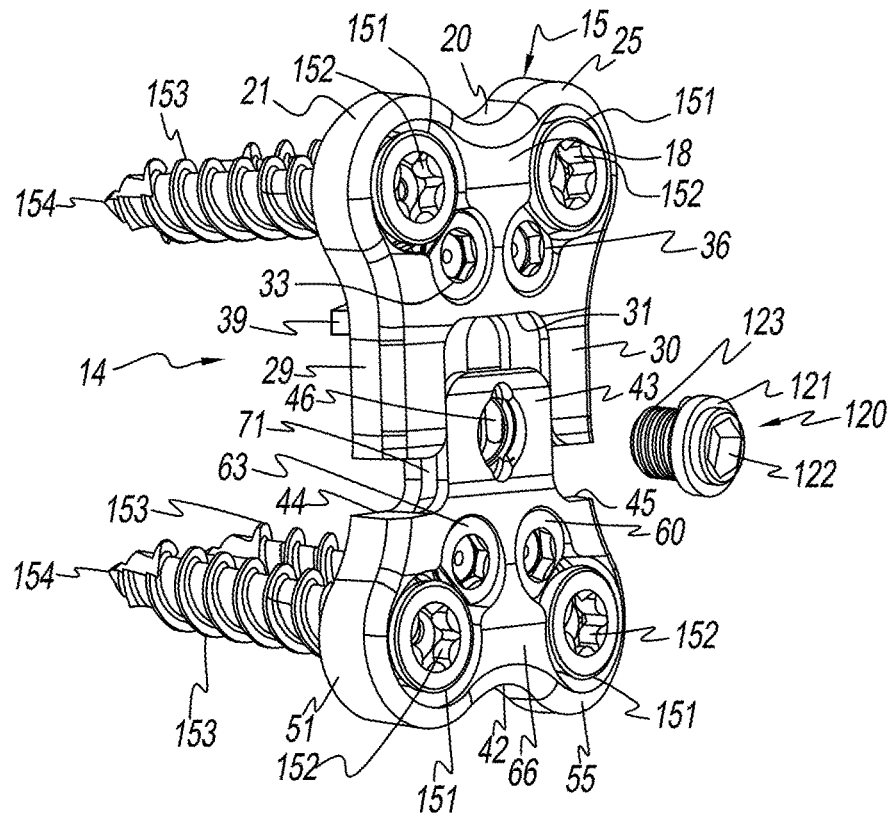
FIG. 17 is a view of the expandable plate in an expanded position with bone screws received by the expandable plate and a threaded locking member shown in exploded view.
Figure 18:
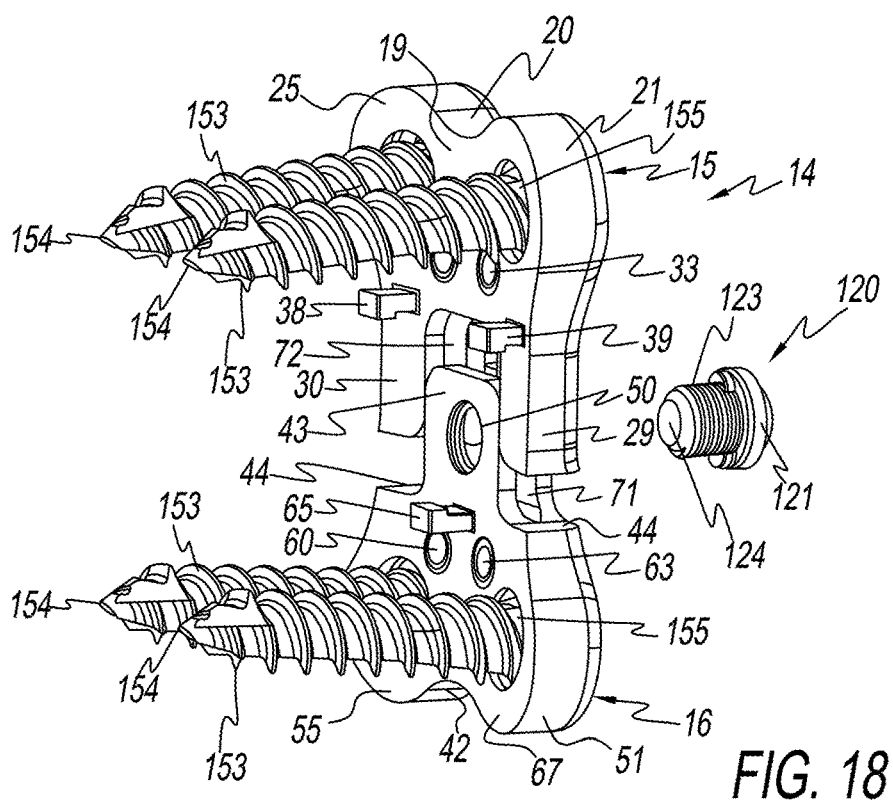
FIG. 18 is a view of the expandable plate in an expanded position with bone screws received by the expandable plate and a threaded locking member shown in exploded view.
Figure 19:
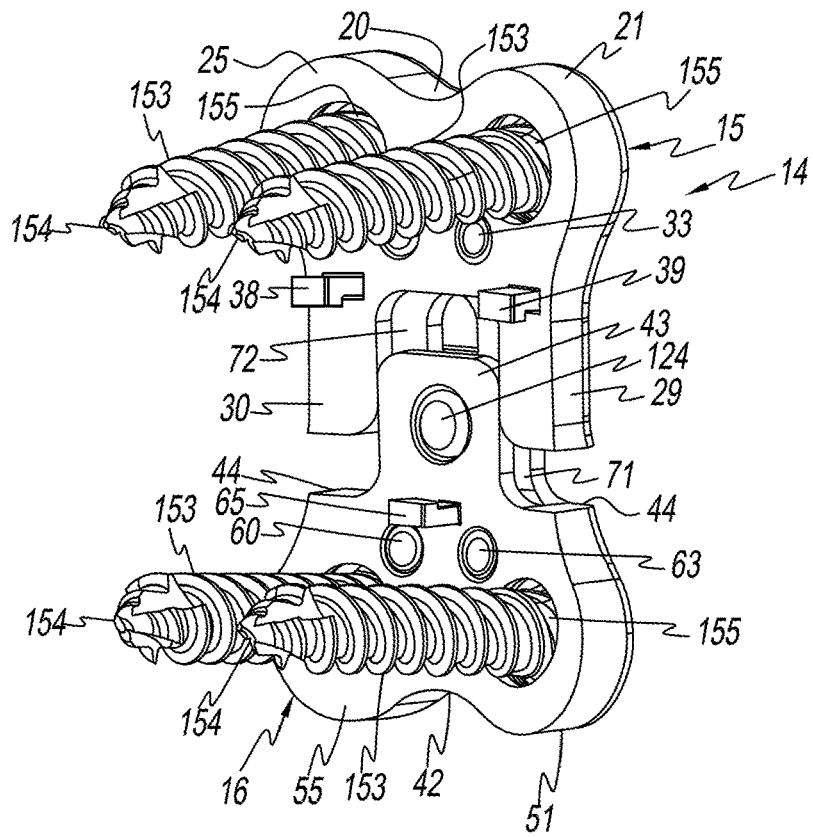
FIG. 19 is a view of the expandable plate in an expanded position with bone screws received by the expandable plate and a threaded locking member received by the expandable plate.

The connection member 120 (shown herein as, but not limited to, a connecting or connection screw 120) is best seen in FIGS. 17-18. The connection screw 120 is formed of a suitable biocompatible material such as those of the cage 12 and the plate 14 as described above, and is made in a same or similar manner. The connection screw 120 provides one manner of connecting or joining the plate 14 to the cage 12. The connection screw 120 has a threaded shaft 123 of a generally cylindrical shape, with a head 121 at one end of the threaded shaft 123, and a tip 124 at an opposite end of the threaded shaft 123. The tip 124 is generally flat. The threaded shaft 123 is sized and configured for reception in the threaded bore 46 of the top/flange 43 of the first portion 16 of the expandable plate 14. The head 121 includes a socket or hole 122 configured to receive an installation tool (not shown) having a complementary portion that is received in the socket 122.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow.

What is claimed is:

1. A spine implant for use between a lower vertebra defining a lower vertebra outer diameter and an adjacent upper vertebra defining an upper vertebra outer diameter, the spine implant comprising:
an expandable intervertebral cage having a first component and a second component slidably engaged and movable relative to the first component, the first component having a first engagement feature, the second component having a second engagement feature; and
an expandable vertebral mounting plate having a first segment defining a first front surface and a first rear surface, and a second segment defining a second front surface and a second rear surface and movable relative to the first segment, the first segment having a first engagement feature configured to engage with the first engagement feature of the first component, the second segment having a second engagement feature configured to engage with the second engagement feature of the second component, the first segment further having a first bone screw bore extending from the first front surface to the first rear surface, the first bone screw bore configured to receive a bone screw that mounts the first segment to the lower vertebra by abutment of the first rear surface of the first segment to the lower vertebra outer diameter, and the second segment further having a second bone screw bore extending from the second front surface to the second rear surface, the second bone screw bore configured to receive a bone screw that mounts the second segment to the upper vertebra by abutment of the second rear surface of the second segment to the upper vertebra outer diameter;
whereby the expandable intervertebral cage and the expandable vertebral mounting plate move as the expandable intervertebral cage is expanded.

2. The spine implant of claim 1, wherein the first engagement feature of the first component is disposed in a bottom of the first component, wherein the second engagement feature of the second component is disposed in a top of the second component, and wherein the second component comprises a third engagement feature disposed in the top of the second component.

3. The spine implant of claim 1, wherein the first engagement feature of the first component of the expandable intervertebral cage comprises a first recess, and the first engagement feature of the first segment of the expandable vertebral mounting plate comprises a first hook.

4. The spine implant of claim 1, wherein the second engagement feature of the second segment of the expandable vertebral mounting plate is situated proximate to a first lateral side of the second segment of the expandable vertebral mounting plate, and wherein the second segment comprises a third engagement feature disposed proximate to a second lateral side of the second segment of the expandable vertebral mounting plate.

5. The spine implant of claim 4, wherein the second engagement feature of the second component of the expandable intervertebral cage comprises a second recess, the second component comprises a third engagement feature comprising a third recess disposed in the top of the second component, the second engagement feature of the second segment of the expandable vertebral mounting plate comprises a second hook, and the third engagement feature of the second segment of the expandable vertebral mounting plate comprises a third hook.

6. The spine implant of claim 1, wherein the first segment of the expandable vertebral mounting plate has a bore for receiving an attachment member for connecting the first segment of the expandable vertebral mounting plate to the first component of the expandable intervertebral cage.

7. The spine implant of claim 1, wherein the first engagement feature of the first segment of the expandable vertebral mounting plate is situated between a first lateral side of the first segment of the expandable vertebral mounting plate and a second lateral side of the first segment of the expandable vertebral mounting plate.

8. The spine implant of claim 1, further comprising a manually operated mechanism for vertically displacing the first component of the expandable intervertebral cage relative to the second component of the expandable intervertebral cage.

9. The spine implant of claim 1, further comprising:
a first cam lock situated in the first segment of the expandable vertebral mounting plate adjacent the first bone screw bore and configured to selectively prevent a first bone screw received in the first bone screw bore from backing out of the first bone screw bore; and
a second cam lock situated in the second segment of the expandable vertebral mounting plate adjacent a third bone screw bore and configured to selectively prevent a third bone screw received in the third bone screw bore from backing out of the third bone screw bore.

10. A spine implant comprising:
an expandable intervertebral cage for implantation between a lower vertebra defining a lower vertebra outer diameter and an adjacent upper vertebra defining an upper vertebra outer diameter of a spine, the expandable intervertebral cage having a first component and a second component movable with respect to the first component, and a displacement mechanism situated between the first component and the second component, the displacement mechanism operative to move the second component relative to the first component, the first component having a first recess and the second component having a second recess; and
an expandable vertebral mounting plate for attachment to the upper vertebra outer surface, the lower vertebra outer surface, and the expandable intervertebral cage, the expandable vertebral mounting plate having a first plate segment and a second plate segment slidably received in the first plate segment, the first plate segment and the second plate segment movable relative to one another to provide a separation between the first plate segment and the second plate segment, the first plate segment having a first hook configured for reception in the first recess of the first component and the second plate segment having a second hook configured for reception in the second recess of the second component, the first plate segment further having a first bone screw bore extending through the first plate segment and configured to receive a bone screw that mounts the first plate segment to the lower vertebra by abutment of the first plate segment to the lower vertebra outer diameter;
whereby the expandable intervertebral cage and the expandable vertebral mounting plate move as the expandable intervertebral cage is expanded.

11. The spine implant of claim 10, wherein the first recess of the first component is disposed in a bottom portion of the first component adjacent a front of the first component, and wherein the second recess of the second component is disposed in a top portion of the second component adjacent a front of the second component.

12. The spine implant of claim 11, wherein the first hook of the first plate segment of the expandable vertebral mounting plate is situated between a first lateral side of the first plate segment and a second lateral side of the first plate segment.

13. The spine implant of claim 12, wherein the second hook of the second plate segment of the expandable vertebral mounting plate is situated proximate to a first lateral side of the second plate segment.

14. The spine implant of claim 10, wherein the first plate segment comprises a second bone screw bore extending through the first plate segment, wherein the first bone screw bore is proximate a first lateral side of the first plate segment and the second bone screw bore is proximate a second lateral side of the first plate segment.

15. The spine implant of claim 14, wherein the first plate segment includes a first plate flange between the first bone screw bore and the second bone screw bore, the first plate flange extending upward from the first plate segment.

16. A spine implant for use between a lower vertebra defining a lower vertebrae outer diameter and an adjacent upper vertebra outer diameter, the spine implant comprising:
   an expandable intervertebral cage comprising:
      a first component having a first recess,
      a second component movable relative to the first component and having a second recess, and
      a displacement mechanism situated between the first component and the second component, the displacement mechanism operative to move the second component relative to the first component; and
   an expandable vertebral mounting plate for attachment to the upper vertebra outer surface, the lower vertebrae outer surface, and the expandable intervertebral cage, the expandable vertebral mounting plate comprising:
   a first plate segment, the first plate segment having a first hook configured for reception in the first recess of the first component,
   a second plate segment movably engaged with the first plate segment, the first plate segment and the second plate segment movable relative to one another to provide a separation between the first plate segment and the second plate segment, the second plate segment having a second hook configured for reception in the second recess of the second component, the second plate segment further having a first bone screw bore extending through the second plate segment and configured to receive a bone screw that mounts the second plate segment to the upper vertebra by abutment of the second plate segment to the upper vertebrae outer diameter,
   whereby the expandable intervertebral cage and the expandable vertebral mounting plate move as the expandable intervertebral cage is expanded.

17. The spine implant of claim 16, wherein the second plate segment comprises a second bone screw bore extending through the second plate segment, wherein the first bone screw bore is proximate a first lateral side of the second plate segment and the second bone screw bore is proximate a second lateral side of the second plate segment.

18. The spine implant of claim 17, wherein the second plate segment comprises a first lateral leg and a second lateral leg, the first lateral leg situated proximate the first bone screw bore and extending downward from the first bone screw bore, and the second lateral leg situated proximate the second bone screw bore and extending downward from the second bone screw bore.

19. The spine implant of claim 18, wherein the first lateral leg and the second lateral leg define a recess between the first lateral leg and the second lateral leg.

20. The spine implant of claim 19, wherein the recess between the first lateral leg and the second lateral leg is configured for reception of a flange of the first plate segment.

* * * * *